United States Patent [19]

Arnold et al.

[11] Patent Number: 5,620,960

[45] Date of Patent: Apr. 15, 1997

[54] USE OF D-ALLOSE AS AN IMMUNOSUPPRESSIVE AGENT

[75] Inventors: Edward C. Arnold, Naperville; Patrick J. Silady, Niles, both of Ill.

[73] Assignee: UOP, Des Plaines, Ill.

[21] Appl. No.: 290,644

[22] Filed: Aug. 15, 1994

[51] Int. Cl.$^6$ .................................................. A61K 31/70
[52] U.S. Cl. ............................................ 514/23; 536/1.11
[58] Field of Search .............................. 536/1.11; 514/23

[56] References Cited

U.S. PATENT DOCUMENTS 4,963,382  10/1990  Arena et al. ............................ 426/548

*Primary Examiner*—Elli Peselev
*Attorney, Agent, or Firm*—Thomas K. McBride; Eugene I. Snyder

[57] ABSTRACT

D-allose has been found to substantially inhibit segmented neutrophil production and to lower platelet counts during in vivo trials, without other significant detrimental clinical effects. Such pharmacological activity makes D-allose a good candidate for treatment, either alone or as an adjuvant, of such conditions as chronic myelogenous leukemia. It also holds promise in reducing thrombus formation during post-operative periods, especially in combination with other anti-clotting drugs.

3 Claims, No Drawings

USE OF D-ALLOSE AS AN IMMUNOSUPPRESSIVE AGENT

FIELD OF THE INVENTION

This application relates to the immunosuppressant activity of D-allose in warm-blooded animals generally, including *homo sapiens*. More particularly this invention relates to the selective, dose-related suppression of segmented neutrophil production by D-allose, where suppression is effected only during the D-allose therapy. More particularly, this invention relates to D-allose as a leukocyte lineage myeloid leukemia suppressant.

BACKGROUND OF THE INVENTION

Although the role of leukocytes in conferring immunity in animals has been recognized since the pioneering experiments of Metchnikoff in 1882, the complexity of the human immune system has been recognized only relatively recently, and an understanding of the complexity of this system has come still later and is continuing. The urgency attending a more complete understanding of the human immune system results not only from the proliferation of acquired immune deficiency syndrome (AIDS) caused by human immunodeficiency viruses (HIV) but also by the realization that there is a broad spectrum of human autoimmune diseases, including rheumatoid arthritis, multiple sclerosis, and myasthenia gravis, where the body's immune system "turns against itself" in a destructive, debilitating fashion. Recent work has generated a plethora of therapeutic regimens directed to regulating and/or controlling one or more portions of the immune system, and the invention within constitutes another addition to the existing arsenal.

That part of the immune system relevant here is limited to the leukocytes derived from the myeloid (bone marrow) portion of the blood. Pluripotent stem cells are thought to be the biological forerunners of all types of blood cells, whether myeloid or lymphoid in origin. It is believed that upon differentiation the pluripotent stem cells generate myeloid stem cells, which are the ancestors of other myeloid progenitor cells. In response to various growth factors the myeloid progenitors further differentiate and mature to give first the so-called precursor cells—cells which are identifiable precursors to mature blood cells—and ultimately mature blood cells. Hematopoiesis—the production of blood cells—from the myeloid line ultimately affords erythrocytes (red blood cells) and the myeloid leukocytes, a heterogeneous mixture of different kinds of white blood cells which embrace monocytes, granulocytes (which include neutrophils, eosinophils, and basophils), and platelets. The platelets are recognized as having a prominent part in the clotting process and, while not related to the immune system, are relevant to our observations. The monocytes, neutrophils and eosinophils are all phagocytes and are the agents of phagocytosis, the process by which a white blood cell "devours" a bacterium, virus, or other kinds of biological debris, and thus play a major role in the body's immune system. Basophils are involved in the inflammatory process which may accompany phagocytosis, but are not otherwise relevant here.

Of the phagocytes listed above the neutrophils are by far the most abundant, constituting roughly 60% of the white blood cells. Short-lived, the neutrophils are the body's first line of defense, reacting swiftly to invading microorganisms or foreign cells generally while the immune system mobilizes other, more specific responses. Neutrophils also secrete substances—lysozymes, beta-glucuronidase and lactoferrins are found in neutrophil primary and secondary granules—which stimulate other immunological responses, thus more completely aligning and enlisting all bodily defenses to foreign matter. Clearly, a significant suppression of neutrophil production decreases the immunological response which a person is capable of mustering. Although normally one wishes to maximize the immune response there are readily recognizable situations where immunosuppression is desirable, with perhaps the outstanding example being organ transplants where the immune system's normal rejection of foreign tissue must be suppressed in order for the tissue ultimately to be accepted.

Another situation where suppression of neutrophil production is desirable is unconnected with the immune system per se and instead is associated with the runaway production of white blood cells characteristic of leukemia. Myeloproliferative disorders refer to certain diseases in which the marrow and sometimes hematopoietic stem cells in extramedullary sites proliferate more-or-less en masse. The proliferation is self-perpetuating. Chronic myelogenous leukemia (CML), sometimes referred to as chronic granulocytic leukemia, is characterized by abnormal proliferation of immature granulocytes—neutrophils, eosinophils, and basophils—in the blood, bone marrow, liver, and sometimes other tissue. The essential feature of CML is the accumulation of granulocytic precursors in the blood, spleen, and marrow. CML arises from a chromosomal defect, where part of chromosome 22 is translocated to the tip of chromosome 9, and vice versa. In such situations it is clearly desirable to suppress the runaway growth of neutrophils as an important segment of the white blood cell population. Acute myelogenous leukemia is characterized by an excess of blast cells, the immediate precursors to neutrophils, and represents another condition which may respond to neutrophil suppression.

What we have discovered through in vivo testing is that D-allose induces a dose-related suppression of segmented neutrophil production and, to a lesser degree, platelet formation. We believe such pharmacological effects can be beneficially employed where suppressing immunological response is desirable, as in organ/tissue transplantation, as well as in myeloproliferative disorders such as CML and others characterized by excessive production of segmented neutrophils. We also have observed that D-allose elicits no other significant physiological response during the period of D-allose administration at dose levels sufficient for immunosuppressant activity. We have further observed that D-allose is excreted largely unchanged. The fact that D-allose is virtually not metabolized while suppressing mature neutrophil and platelet production has significant consequences regarding the scope of D-allose activity.

We believe that the significant reduction in platelet formation also can be therapeutically utilized, especially where D-allose is used as an adjuvant, i.e., in conjunction with other medication to facilitate the latter's effectiveness. For example, platelet reduction may be generally desirable to avoid thrombus formation in a variety of post-operative scenarios, where D-allose delivery in conjunction with an anticoagulant such as heparin might form a particularly effective treatment. Thrombocytosis and thrombocythemia also are conditions characterized by an elevated platelet count which might respond to D-allose treatment. It is interesting that primary thrombocythemia may accompany or evolve into chronic myelogenous leukemia; see "Cecil Textbook of Medicine," 18th Ed., J. B. Wyngaarden and L. H. Smith, Jr., Editors, 1988 (W. B. Saunders Co.), page 1054.

Finally, it needs to be noted that our observed effect by D-allose on neutrophil and platelet production appears to be quite specific, and without any obvious detrimental side effects typical of the current leukemia therapeutic agents. This is a significant distinction having great practical consequences.

SUMMARY OF THE INVENTION

The purpose of this invention is to provide a method of suppressing leukocyte formation in warm blooded animals. More particularly, our invention is a method of suppressing immunological response associated with leukocyte activity comprising administering D-allose in a pharmaceutically acceptable preparation. In another variant our invention is a method of treating chronic myelogenous leukemia by administering a pharmaceutically acceptable preparation of D-allose in an amount effective to suppress formation of segmented neutrophils. Our invention also is a method of inhibiting platelet formation in the blood stream. Other embodiments will be apparent from the ensuing description of our invention.

DESCRIPTION OF THE INVENTION

Our invention is based on the observation that D-allose when administered to rats evokes a dose-related suppression of segmented neutrophil production, along with a lower suppressive effect on platelet production, where the suppressive effect remains only so long as D-allose administration is continued. This in vivo response is unaccompanied by any observed harmful, or potentially harmful, side effects. We believe such pharmacological activity has broad consequences not only in the treatment of chronic myelogenous leukemia, but also in suppressing immune response in, for example, organ or tissue transplants.

D-allose is a ketohexose which is dextrorotatory and of the same stereochemical series as D-glyceraldehyde. Thus, D-allose has the absolute configuration designated as (R) at C-5, that is, the stereocenter most distant from the carbonyl group. D-allose differs from the more familiar D-glucose only in having the stereochemistry at C-3 opposite to that found in D-glucose. Contrary to the situation with D-glucose, D-allose is a rare ketohexose, which means that it occurs naturally only in very limited amounts. However, conversion of D-glucose to D-allose can be effected, providing the availability of this monosaccharide by a synthetic route.

We have found that D-allose may be safely administered to warm blooded animals. Mutagenic and acute oral toxicity tests indicated no adverse characteristics.

EXAMPLE 1

Safety Studies

Several studies showed that D-allose consumption posed no obvious health issues.

Mutagenicity Tests

D-allose showed no mutagenic properties in the following assays:
1) salmonella/mammalian—microsome reverse mutation assay;
2) mouse lymphoma forward mutation assay;
3) chromosomal aberrations in chinese hamster ovary cells;
4) in vitro transformation of Balb cells;
5) sister chromatid exchange in human lymphocytes with and without activation.

Acute Oral Toxicity Study in Male Rats

At 5 grams grams/Kg no mortalities, no remarkable body weight changes, no pharmacotoxic signs and no visible post-mortem abnormalities.

Oral and Intravenous D-allose Primate Study

With six successive daily oral doses (0.34 g/Kg), no ill effects with essentially complete elimination of D-allose in urine. With single 0.2 g/Kg intravenous dose, no ill effects and essentially complete elimination in urine.

With the safety of D-allose established by the foregoing screening tests, a more extensive program to determine the bioactivity of D-allose was conducted.

EXAMPLE 2

D-allose Bioactivity

D-allose or deionized water was administered to 15 male and 15 female rats (Crl:CD®BR rats approximately 4 weeks of age from Charles River Laboratories) by gavage once daily for 28 days at dosage levels of D-allose of 3.1 and 5.1 g/Kg/day. The control animals received deionized water at a dosage volume comparable to the test animals.

Each rat was observed twice daily for mortality, morbidity and overt signs of toxicity. Detailed observations were performed once during each study week. Individual body weights, food consumption, food efficiency and water consumption were recorded daily. Hematology, biochemistry and urinalysis evaluations were conducted on all male and female animals during the last week of study. At study termination, all animals were euthanized. The animals had a thorough post-mortem examination conducted. A complete set of major tissues and organs was harvested and selected organ weights were determined. Protocol-specified tissues were processed histologically and microscopic examination was conducted. There were no D-allose-related effects on survival, appearance, behavior, body weights, food consumption or water consumption.

Hematological studies showed a marked decrease in segmented neutrophils which was dose-related and associated with a marked reduction in mature myeloid cells in the bone marrow smears. Platelets also showed a dose-related reduction in numbers in both sexes. There was no apparent effect on the erythroid series.

Mortality

The rats were observed for morbidity and mortality at least twice daily throughout the study.

Clinical Signs

The rats were observed twice daily for signs of overt toxicity at the times of the morbidity/mortality checks. Detailed observations were conducted once each study week during the 28 days of the study. There was no definitive D-allose-related effect on appearance or behavior among any of the treatment groups.

Body Weights

Individual body weights were recorded daily for the 28 days of the study. Body weights for the treatment animals were comparable to those of the control group. Body weights of the male and female D-allose 5.1 g/Kg/day treated group were lower than the control group, but the differences in mean values were not statistically significant.

Food Consumption And Food Efficiency

For the first 28 days of the study, individual food consumption was recorded daily and food efficiency was calculated. There was no D-allose-related effect on mean food consumption values or mean food efficiency values during the study. Increases and decreases occurred in food efficiency values for males and females at all treatment levels, with no obvious trend.

Water Consumption

Individual water consumption was recorded daily for the 28 days of the study. There was no D-allose-related effect on mean water consumption values.

Clinical Pathology

Clinical laboratory studies were conducted on all main animals at termination of study. Blood samples were obtained from the orbital sinus following an overnight fasting period in which water was available. Urine was collected during the fasting period.

Hematology

Hemhtological values are summarized in Tables 1 and 2. The main findings were of a dose-related reduction in platelet counts in both sexes and a reduction in segmented neutrophils associated with reductions in total leukocyte counts. Segmented neutrophils were very low or not countable in some high dose group animals. As a result, bone marrow smears were examined for all animals.

TABLE 1

| | | Males: Summary of Hematological Values | | | | | | | |
|---|---|---|---|---|---|---|---|---|---|
| Parameters | Day of | 0 g/kg/day (Control) | | | D-allose 3.1 g/kg/day | | | D-allose 5.1 g/kg/day | | |
| Measured | Study | MEAN | S.D.[d] | N[e] | MEAN | S.D. | N | MEAN | S.D. | N |
| Segmented Neutrophils × $10^3$/cmm | Terminal | 1.9 | 1.58 | 5 | 0.9 | 0.51 | 5 | 0.2 | 0.15 | 5 |
| Band Neutrophils × $10^3$/cmm | Terminal | 0.0 | 0.00 | 5 | 0.0 | 0.00 | 5 | 0.0 | 0.00 | 5 |
| Lymphocytes × $10^3$/cmm | Terminal | 7.4 | 1.13 | 5 | 9.1 | 2.44 | 5 | 5.6 | 1.48 | 5 |
| Eosinophils × $10^3$/cmm | Terminal | 0.2 | 0.19 | 5 | 0.1 | 0.17 | 5 | 0.1 | 0.04 | 5 |
| Monocytes × $10^3$/cmm | Terminal | 0.2 | 0.13 | 5 | 0.1 | 0.04 | 5 | 0.1 | 0.08 | 5 |
| Basophils × $10^3$/cmm | Terminal | 0.0 | 0.00 | 5 | 0.0 | 0.00 | 5 | 0.0 | 0.00 | 5 |
| Other Cells × $10^3$/cmm | Terminal | 0.0 | 0.00 | 5 | 0.0 | 0.00 | 5 | 0.0 | 0.00 | 5 |
| Leukocytes × $10^3$/cumm | Terminal | 9.6 | 2.33 | 5 | 10.3 | 2.09 | 5 | 5.9[b] | 1.51 | 5 |
| Erythrocytes × $10^6$/cumm | Terminal | 6.85 | 0.556 | 5 | 7.10 | 0.442 | 5 | 7.03 | 0.339 | 5 |
| Platelets × $10^3$/cmm | Terminal | 1072 | 152.7 | 5 | 546[c] | 233.9 | 5 | 320[c] | 83.6 | 5 | b. Significantly different from the control group; $p \leq 0.5$
c. Significantly different from the control group; $p \leq 0.01$
d. Standard Deviation
e. Number of Animals

TABLE 2

| Parameters Measured | Day of Study | 0 g/kg/day (Control) | | | D-allose 3.1 g/kg/day | | | D-allose 5.1 g/kg/day | | |
|---|---|---|---|---|---|---|---|---|---|---|
| | | MEAN | S.D. | N | MEAN | S.D.[d] | N[e] | MEAN | S.D. | N |
| Segmented Neutrophils × 10³/cmm | Terminal | 1.8 | 0.93 | 5 | 0.5 | 0.30 | 5 | 0.1 | 0.15 | 5 |
| Band Neutrophils × 10³/cmm | Terminal | 0.0 | 0.00 | 5 | 0.0 | 0.00 | 5 | 0.0 | 0.00 | 5 |
| Lymphocytes × 10³/cmm | Terminal | 7.6 | 1.97 | 5 | 5.8 | 1.34 | 5 | 5.2 | 0.59 | 5 |
| Eosinophils × 10³/cmm | Terminal | 0.1 | 0.19 | 5 | 0.1 | 0.11 | 5 | 0.1 | 0.04 | 5 |
| Monocytes × 10³/cmm | Terminal | 0.1 | 0.11 | 5 | 0.1 | 0.08 | 5 | 0.0 | 0.05 | 5 |
| Basophils × 10³/cmm | Terminal | 0.0 | 0.00 | 5 | 0.0 | 0.00 | 5 | 0.0 | 0.00 | 5 |
| Other Cells × 10³/cmm | Terminal | 0.0 | 0.00 | 5 | 0.0 | 0.00 | 5 | 0.0 | 0.00 | 5 |
| Leukocytes × 10³/cumm | Terminal | 9.6 | 2.81 | 5 | 6.5 | 1.33 | 5 | 5.4 | 0.57 | 5 |
| Erythrocytes × 10⁶/cumm | Terminal | 6.17 | 0.626 | 5 | 6.24 | 0.462 | 5 | 6.42 | 0.324 | 5 |
| Platelets × 10³/cmm | Terminal | 992 | 149.4 | 5 | 567[c] | 91.3 | 5 | 414[c] | 174.3 | 5 | b. Significantly different from the control group; $p \leq 0.5$
c. Significantly different from the control group; $p \leq 0.01$
d. Standard Deviation
e. Number of Animals Biochemistry Cholesterol was significantly increased only in male animals at the high dose level (72 vs. 51 mg/dl). The other minor changes seen were not considered to be biologically meaningful. Urine volumes were decreased in the treated groups while specific gravity was increased. pH was decreased in treated animals.

Bone Marrow

Bone marrow cytological preparations from animals in the control and both treatment groups were very cellular with adequate numbers of active megakaryocytes in varying stages of maturity. Erythroid series in all groups appeared well represented with a normal maturation sequence.

Animals in the control groups had predominantly late stage (mature and band forms) neutrophils with lower numbers of mature and band eosinophils. Both of these granulocytic series had normal maturation sequences. Myeloid to erythroid ratios ranged from approximately 1.6 to 3.0 with males typically on the higher end and females toward the lower end of this range. Lymphoid, mast cells and other mononuclear cells were present in normal numbers and maturational stages.

Animals from the low and high dosage groups (3.1 and 5.1 g/kg/day, respectively) had decreased numbers of late stage neutrophils. The decreases were most striking in the high dose groups and generally were consistent with neutrophil numbers in the peripheral blood. An overall decrease in cytological integrity of the cells in the neutrophil series was noted in both dosage groups and prevented accurate identification of many cells. Myeloid to erythroid ratios in bone marrows from both treatment groups were usually less than 1.0.

Anatomic Pathology

There were no treatment related findings at necropsy or on histopathological examination of the following organs.

Adrenal Gland, Cortex
Adrenal Gland, Medulla
Brain
Epididymis
Esophagus
Eye
Eye, Optic Nerve
Heart
Kidney
Large Intestine, Cecum
Large Intestine, Colon
Large Intestine, Rectum
Liver
Lymph Node, Iliac
Lymph Node, Renal
Pancreas
Parathyroid Gland
Small Intestine, Duodenum
Small Intestine, Ileum
Small Intestine, Jejunum
Spleen
Stomach, Glandular
Stomach, Nonglandular
Testis
Thyroid Gland
Urinary Bladder The foregoing data show a dose-related reduction in segmented neutrophil production associated with the failure of precursor neutrophil cells to mature into segmented neutrophils. Associated with the reduction in neutrophil count was a significant reduction in platelet formation.

Further studies on the metabolic fate of D-allose provided the quite surprising result that this monosaccharide is not metabolized to a significant degree, which corroborates results previously reported in U.S. Pat. No. 4,963,382.

EXAMPLE 3

D-allose Excretion Routes

This study was patterned after that Example 1 where a satellite group of animals received radiolabeled D-allose to establish excretion routes. On day 28, the animals in the satellite groups (5 controls, 5 males and 5 females) received a single dose of [$^{14}$C]D-allose for-study days 1–28 at the same dose concentration as the non-radiolabeled material except for the "Control Satellite Group" which received a single high dose containing radiolabeled D-allose.

On days 1–27, all control group animals (main and satellite) received deionized water at the same dosage volume as the test animals. However, on day 28 the satellite control animals became "Unadapted High Dose Test Animals" in that they received a high dose (5.1 g/kg) of radiolabeled D-allose. In this manner the "Unadapted High Dose Test Animals" could be directly compared to the multiple high dose animals which were adapted by administration of the high dose for 28 days.

Each rat was observed twice daily for mortality, morbidity and overt signs of toxicity. Detailed observations were performed once during each study week. Individual body weights, food consumption, food efficiency and water consumption were recorded daily. Urine and expired air were collected from the animals in the satellite groups at 6, 12, 24, 48, 72 and 96 hours following radiolabeled dosing. Feces samples were collected at 24, 48, 72 and 96 hours after radiolabeled dosing from the satellite group animals. Duplicate aliquots of expired air solution, urine, feces and cage wash were analyzed by liquid scintillation counting (LSC). At study termination, all animals were euthanized. The carcasses from the satellite groups were analyzed for radioactive content only. There were no D-allose-related effects on survival, appearance, behavior, body weights, food consumption or water consumption.

The studies with radiolabeled D-allose showed that most of the radioactivity was excreted in the urine with a small amount in the feces and lesser amounts in exhaled air and retained in the carcass. When expressed as a fraction of the administered dose, urinary excretion in males was about 84 percent in the unadapted high dose (control) group, 96 percent in the 3.1 g/kg/day group and 73 percent in the 5.1 g/kg/day group. In females the values in urine were 103 percent, 79 percent and 72 percent, respectively for animals in the same dosage groups.

Excretion in the feces was much lower than urine. For feces the average amounts of radioactivity for the unadapted high dose (control), low and high dose groups were 13, 6 and 10 percent in males and 3, 9 and 5 percent in females. Radiation in exhaled air (between hours 0–8) was less than 0.5 percent in all groups while the carcass retained less than 1 percent.

The average total recovery of the radioactive dose administered was quite variable. The total fraction of the administered dose which was recovered ranged from 81±5% for the high dose females (Group 6) to 109±2% of the dose for the unadapted high dose (Group 4) females.

When corrected for the recovery of radioactivity in each group, urinary excretion averaged approximately 90% of the recovered dose and was equivalent for all three test groups. When corrected for recovery the excretion of radiolabel in the feces ranged from 6 to 9% of the recovered dose.

Based on these results, no substantial differences in the rates or routes of excretion were noted between any of the treatment groups which were administered radiolabeled D-allose.

HPLC (High Pressure Liquid Chromatography) of urine from treated animals was compared with $C^{14}$ radiolabeled D-allose spiked urine from control animals. The treated animal urine HPLC chromatographs exhibited a major peak corresponding to the spiked D-allose peak in the control urine. An independent specific assay for D-allose confirmed the presence of undigested D-allose in the urine of the treated animals.

The confirmation by the foregoing study that little, if any, D-allose is metabolized in the body is remarkable in the context of the significant and profound pharmacological activity of D-allose. Although we do not yet know the detailed biochemical basis of the D-allose pharmacological activity, carbohydrates generally are known to be key components of cell walls and are believed to be the primary markers for cell recognition. See N. Sharon and H. Lis, *Scientific American,* Jan., 1993, pp. 82–89. It also is known that there is a class of a proteins called lectins which bind specifically to particular carbohydrates. Thus, there is ample biochemical evidence of specific protein binding to cell surfaces mediated by carbohydrates present on, or incorporated in, the cell wall. Continuing with this speculative, hypothetical reasoning one easily could postulate that the presence in the bloodstream of a carbohydrate otherwise incorporated as a cell marker now selectively will bind with a protein seeking that carbohydrate as a cell marker, and thus interfere with the normal biochemical activity mediated by the protein or enzyme. In this way, it is unnecessary for the carbohydrate to be metabolized in order for it to have significant pharmacological activity.

This also has far reaching consequences for the types of compounds which can exhibit the same effects as, for example, D-allose. For if the D-allose merely acts as a specific binding site for a protein, thereby blocking its action, it then follows that similar activity can be expected to be expressed in compounds incorporating D-allose. Thus, one reasonably can expect nucleotides, nucleosides, glycoproteins, glycolipids, and oligosaccharides incorporating D-allose to manifest significant D-allose activity in suppressing segmented neutrophil production. In this application we shall use the phrase "pharmacologically active variant of D-allose" to indicate all of the foregoing classes of compounds containing D-allose as a part thereof and which exhibit significant D-allose activity in reducing segmented neutrophil production.

A pharmaceutical preparation according to our invention comprises D-allose or a pharmacologically active variant of D-allose contained in a pharmaceutically acceptable form. For treatment purposes, a pharmaceutical preparation according to our invention may be administered orally, parenterally, or directly into the tissue in which the maturation of myeloid precursor takes place, i.e., into the bone marrow. Effective doses may depend on the kind and the severity of the condition which exists or the response to be elicited but may vary from between about 0.01 g/Kg/day up to about 6g/Kg/day when administered orally, and correspondingly lower doses when administered parenterally or injected directly into the bone marrow. The pharmaceutical preparation also may contain conventional pharmaceutically acceptable carriers that are suitable for the particular mode of administration and which do not deleteriously interact with D-allose or the pharmacologically active variant thereof. Since D-allose shows high water solubility aqueous media are particularly suitable pharmaceutical carriers. Thus, D-allose or a pharmacologically active variant thereof may be combined with a pharmacological carrier, such as a suitable liquid vehicle or excipient and an optional auxiliary additive or additives. The liquid vehicles and excipients are conventional and commercially available.

What is claimed is:

1. A method of suppressing formation of segmented neutrophils in warm blooded animals comprising administering to warm-blooded animals in need thereof an effective dose of a pharmaceutical preparation of D-allose.

2. A method of treating a warm blooded animal having a disease resulting from segmented neutrophil activity comprising administering to warm-blooded animals in need thereof an effective dose of a pharmaceutical preparation of D-allose.

3. A method of suppressing formation of platelets in warm blooded animals comprising administering to warm-blooded animals in need thereof an effective dose of a pharmaceutical preparation of D-allose.

* * * * *